United States Patent [19]

Polymeropoulos et al.

[11] Patent Number: 5,369,004

[45] Date of Patent: Nov. 29, 1994

[54] FIVE HIGHLY INFORMATIVE MICROSATELLITE REPEAT POLYMORPHIC DNA MARKERS

[75] Inventors: Mihael H. Polymeropoulos, Potomac; Carl R. Merril, Rockville, both of Md.

[73] Assignee: The United States of America as represented by the Department of Health and Human Services, Washington, D.C.

[21] Appl. No.: 922,723

[22] Filed: Jul. 31, 1992

Related U.S. Application Data

[63] Continuation-in-part of Ser. No. 799,828, Nov. 27, 1991, which is a continuation-in-part of Ser. No. 707,501, May 29, 1991, abandoned.

[51] Int. Cl.$^5$ .................. C12Q 1/68; C12P 19/34; C07H 21/04
[52] U.S. Cl. .......................... 435/6; 435/91.2; 536/24.31; 536/24.33
[58] Field of Search ................ 435/91.2, 6; 536/24.33, 536/24.31

[56] References Cited

U.S. PATENT DOCUMENTS

| | | | |
|---|---|---|---|
| 4,683,195 | 7/1987 | Mullis et al. | 435/91 |
| 4,683,202 | 7/1987 | Mullis | 435/91 |
| 4,800,159 | 6/1989 | Mullis et al. | 435/91 |
| 4,879,214 | 11/1989 | Kornher et al. | 435/6 |
| 5,001,050 | 3/1991 | Blanco et al. | 435/6 |

OTHER PUBLICATIONS

Klobeck et al. (1987) Nucl. Acids Res. vol. 15 "N Segment Insert & Region-Directed Somatic Hypermutation in a Kappa Gene of a t(2;8)Chromosomal Translocation", pp. 4877–4888.

Nomiyama et al. (1984) Nucl. Acids Res., vol. 12, "Interruption of a Human Nuclear Sequence Homologous to Mito. DNA by a Member of the Kpnl 1.8Kb Family" pp. 5225–5234.

Dull et al. (1984) Nature, vol. 310, "Insulin–Like Growth Factor II Precursor Gene Organization in Relation to Insulin Gene Family", pp. 777–781.

Dean et al. (1990) Nucl. Acids Res., vol. 18, "Approaches to Localizing Disease Genes as Applied to Cystic Fibrosis", pp. 346–350.

Boylan et al. (1990) Genomics, vol. 6, "Repetitive DNA (TGGA)$_n$ 5' to the Human Myelin Basic Protein Gene: A New Form of Oligo. Repetitive Sequence Showing Length Polymorphism.", pp. 16–22.

(List continued on next page.)

*Primary Examiner*—Mindy B. Fleisher
*Attorney, Agent, or Firm*—Lowe, Price, LeBlanc & Becker

[57] ABSTRACT

The invention relates to polymorphic markers (two tetranucleotide, one dinucleotide repeat polymorphisms, 27 markers characterized by primer pairs 1A–27A, and five markers characterized by primer pairs 1B–5B that are useful for human individualization. Applications are in forensic medicine and for paternity and prenatal screening as well as genetic mapping. These markers are characterized by sets of oligonucleotide primers according to the invention useful in PCR amplification and DNA segment resolution. The invention further relates to an assay for measuring the subtle differences in genetic material regarding an added or omitted set of dinucleotide or tetranucleotide repeat polymorphisms which comprises obtaining an amount of nucleotide segments effective for testing, amplifying the segments by the PCR procedure using at least one primer nucleotide sequence according to the present invention, resolving the amplified segments using gel electrophoresis, and comparing the resolved segments by autoradiography to observe the differences in migration patterns due to structural differences. The assay according to the invention is easy to perform and results can be obtained within 24 hours. It is not uncommon for results to be available within 3–4 hours. Accordingly, the invention also relates to an improved PCR procedure and a PCR assay kit which comprise nucleotides according to the invention.

4 Claims, 9 Drawing Sheets

OTHER PUBLICATIONS

Kirkness et al. (1991) Genomics, vol. 10, "Isolation, Characterization, Localization of Human Genomic DNA Encoding the Beta 1 Subunit of the $GABA_A$ Receptor (GABRBl)", pp. 985–995.

Vihko et al. (Aug. 1988) FEBS Lett, vol. 236, "Molecular Cloning and Sequence Analysis of cDNA Encoding Human Prostatic Acid Phosphatase", pp. 275–281.

Weber et al, Abundant Class of Human DNA Polymorphisms Which can be Typed Using the Polymerase Chain Reaction, Am. Hum. Genet., vol. 44, pp. 388–396 (1989).

Moos et al, "Structure of Two Human Beta-Actin-related Processed Genes One of Which is Located Next to a Simple Repetitive Sequence", EMBO Journal, vol. 2, No. 5, pp. 757–761, (1983).

Chen et al., "The Human Growth Hormone Locus: Nucleotide Sequence, Biology, and Evolution", Genomic, vol. 2, pp. 479–497 (1989).

Engelke et al, Direct sequencing of enzymatically amplified human genomic DNA, Proc. Natl. Acad. U.S.A., vol. 85, pp. 544–548 (1988).

Wong et al, Characterization of $\beta$-thalassemia mutations using direct genomic sequencing; of amplified single copy DNA, Nature, vol. 330, pp. 384–386 (1987).

Botstein et al, Construction of a Genetic Linkage Map in Man Using Restriction Fragment Length Polymorphisms Am. J. Hum. Genet., vol. 32, pp. 314–331 (1980).

White et al, Chromosome Mapping with DNA Markers, Scientific American, vol. 258, pp. 40–48 (1988).

Wallace et al, The use of synthetic oligonucleotides as hybridization probes. II Hybridization of oligonucleotides of mixed sequence to rabbit $\beta$-globin DNA, Nucl. Acid Research, vol. 9, pp. 879–894 (1981).

Litt et al, A Hypervariable Microsatellite Revealed by In Vitro Amplification of a Dinucleotide Repeat within the Cardiac Muscle Actin Gene, Human Genet, vol. 44, pp. 397–401 (1989).

Weber et al, Dinucleotide Repeat Polymorphism at the D12S43 Locus, Nucleic Acids Research, vol. 18, No. 15, p. 4637.

Tautz et al, Nucleic Acids Research, vol. 12, No. 10, 1984, pp. 4127–4138.

Nakamura et al, Variable Number of Tandem Repeat (VNTR) Markers for Human Gene Mapping, Science, vol. 235, 2987, pp. 1616–1622.

Jeffreys et al, Spontaneous Mutation Rats to New Length Alleles at Tandem-Repetitive Hypervariable Loci in Human DNA, Nature, vol. 332, 1988, pp. 278–281.

Overhauser et al, Nucleic acids Research, vol. 15, No. 11, 1987, pp. 4617–4627.

Jeffreys et al, Hypervariable "minisatellite" regions in Human DNA, Nature, vol. 314, 1985, pp. 67–73.

Dariavach et al., "Human Ig Superfamily CTLA-4 Gene: Chromosomal Localization and Identity of Protein Sequence Between Murine and Human CTLA-4 Cytoplasmic Domains", European Journal of Immunology, vol. 18, pp. 1901–1905 (1988).

FIGURE 1

AATCTGGGCG ACAAGAGTGA             20

FIGURE 2

ACATCTCCCC TACCGCTATA             20

FIGURE 3

TCCAGCCTCG GAGACAGAAT             20

FIGURE 4

AGTCCTTTCT CCAGAGCAGG T           21

FIGURE 5

GCCAGTGATG CTAAAGGTTG             20

FIGURE 6

AACATACGTG GCTCTATGCA             20

FIGURE 7

```
AATCTGGGCG ACAAGAGTGA AACTCCGTCA AAAGAAAGAA AGAAAGAGAC    50
AAAGAGAGTT AGAAAGAAAG AAAGAGAGAG AGAGAGAAAG GAAGGAAGGA   100
AGAAAAAGAA AGAAAAAGAA AGAAAGAGAA AGAAAGAAAG AGAAAGAAAG   150
AAAGAAAGAA AGAAAGAAAG AAAGAAAGAA AGAAAGAAAA AGAAAGAAAG   200
AAAGAAAGAA AGAAAGAAAG AAAGAAAGAA AGAAAGAAAG AAAGAAAGGA   250
AGGAAAGAAA GAGCAAGTTA CTATAGCGGT AGGGGAGATG T            291
```

FIGURE 8

```
GCCAGTGATG CTAAAGGTTG TATTGCATAT ATACATATAT ATATATATAT    50
ATATATATAT ATATATATAT ATATATATAT ATATATATAT TTTAATTTGA   100
TAGTATTGTG CATAGAGCCA CGTATGTT                           128
```

FIGURE 9

```
TCCAGCCTCG GAGACAGAAT GAGACTCCAT CAAAAACAAG AAAGAAAGAA    50
AGACAAAGAG AGAAAGAAAG AAAGAAAGAA AGAAAGAAAG AGAGAGAG    100
AGAGAGAGAG AGAAAGAAAG AAAGAAAGAA AGAAAGAAAG AAAGAAAGAA   150
AGAAAGAAAG AAAGAAAGAA GGAAAGAAAG AAAGGAAACT AAAATAACTA   200
AATAACTGAG TAGCACCACA CCACCTGCTC TGGAGAAAGG ACT          243
```

FIGURE 10

```
TTTCTGGGTG TGTCTGAAT                                      19
```

FIGURE 11

```
ACACAGTTGC TCTAAAGGGT                                     20
```

FIGURE 12
CTAGGTTGTA AGCTCCATGA                    20

FIGURE 13
TTGAGCACTT ACTCTGTGCC                    20

FIGURE 14
AACTCAGAAC AGTGCCTGAC                    20

FIGURE 15
ATTTCCCTCA AGGCTCCAGG T                  21

FIGURE 16
CTGATCTTGC TCACCTTCGA                    20

FIGURE 17
GCGTTTGCTG AAATGAAGGA                    20

FIGURE 18
GCAGGTACTT AGTTAGCTAC                    20

FIGURE 19
TTACAGTGAG CCAAGGTCGT                    20

FIGURE 20
TTTGTCTGGA TAGACTGGAG                    20

FIGURE 21

CCATCTTCCT GTGGCTGTA                    19

FIGURE 22

CTAATGCAGA GATTTAGGGC                   20

FIGURE 23

GTGGTGTAAA GACTGCATAG                   20

FIGURE 24

ATGTGACTGA TGTGGGTCAG                   20

FIGURE 25

CATCTGCACT CATGCTCCAT                   20

FIGURE 26

TCCCAGATCG CTCTACATGA                   20

FIGURE 27

CACAGCTTCA GAAGTCACAG                   19

FIGURE 28

GAGCAATGTT GCTTAGGATG                   20

FIGURE 29

TGGAAGTGTC ACTGGCATGT                   20

FIGURE 30

TGTGTCCAGC CTTAGTGTGC A    21

FIGURE 31

TCATCACTTC CAGAATGTGC    20

FIGURE 32

ACTGCCTCAT CCAGTTTCAG    20

FIGURE 33

GAGCAGGCAC TTGTTAGATG    20

FIGURE 34

CCTCTTGGCT CTAACAGCAA    20

FIGURE 35

AGCAAGACCC TGTCTCAAGA    20

FIGURE 36

CAAGGCCCAT CTTCAGTAGA    20

FIGURE 37

CCTTCTCACT CCTTTACTAG    20

FIGURE 38

GAAGACTGAG GAGGTCAGAA    20

FIGURE 39
CTACTGTTCA GAGTCAAAGC   20

FIGURE 40
TGCCCCACAT TAGGATGCAT   20

FIGURE 41
AGGGACACGA ATCAGATCAG   20

FIGURE 42
GTGGTACCTC ATTGTGGCTA   20

FIGURE 43
AGGCATCCTT GTGCTGACAT   20

FIGURE 44
TTTGGCCGAC AGTGGTGTAA   20

FIGURE 45
AGGACCAAAC CATGTCTGTC   20

FIGURE 46
CTGCATCTGA GCATATGGGA   20

FIGURE 47
CATTCAGACT ATGCAGGCTT   20

FIGURE 48

CTGGGACTAC TGGCACATG             19

FIGURE 49

GGCAACGTGG TGAAACCTT             19

FIGURE 50

GGAAGATGGA GTGGCTGTTA            20

FIGURE 51

CTCCAGCCTG GCGAAAGAAT            20

FIGURE 52

GTAAGACTTT TGGAGCCATT            20

FIGURE 53

TTCAGGGAGA ATGAGATGGG            20

FIGURE 54

GACAGAGTGA GACTCCATCT            20

FIGURE 55

GATCCTATCT TCTCAGGAGG            20

FIGURE 56

GAGGTTGCAC TCCAGCCTTT            20

FIGURE 57

ATGCCATGCA GATTAGAAA                    19

FIGURE 58

GGAAAGAAAC AGTGAAAGA                    19

FIGURE 59

ATCCATCGAC CTCTGGGTTA                   20

FIGURE 60

GACCCCACAG CCTATTCAGA                   20

FIGURE 61

TTGACTGCTG AACGGCTGCA                   20

FIGURE 62

CAGCTGCCCT AGTCAGCAC                    19

FIGURE 63

GCTTCCGAGT GCAGGTCACA                   20

FIGURE 64

GGGCAACATG GTGAAACCTT                   20

FIGURE 65

CCTAGCCTAT ACTTCCTTTC                   20

FIGURE 66

GGACCTCGTG AATTACAATC                    20

FIGURE 67

ATTTACCTAC CTGTTCATCC                    20

FIGURE 68

TTGTGTCAAC TGCTGATATG                    20

FIGURE 69

AACCAAAACA TCATTCCCTA                    20

FIGURE 70

CGTAAGCGTG CACTATACCC T                  21

FIGURE 71

CTGAGGATTC ATCCACCTG                     19

FIGURE 72

CCTGAGTAGC TGTTAAGGGA                    20

FIGURE 73

GCACATGTAC CCTAGAACTT                    20

SEQUENCE LISTING ( 1 ) GENERAL INFORMATION:

( i i i ) NUMBER OF SEQUENCES: 73

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AATCTGGGCG ACAAGAGTGA        20

( 2 ) INFORMATION FOR SEQ ID NO:2:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ACATCTCCCC TACCGCTATA        20

( 2 ) INFORMATION FOR SEQ ID NO:3:

( i ) SEQUENCE CHARACTERISTICS:
        ( A ) LENGTH: 20

(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

TCCAGCCTCG GAGACAGAAT                       20

(2) INFORMATION FOR SEQ ID NO:4:

(i) SEQUENCE CHARACTERISTICS:
    (A) LENGTH: 21
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

AGTCCTTTCT CCAGAGCAGG T                     21

(2) INFORMATION FOR SEQ ID NO:5:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

GCCAGTGATG CTAAAGGTTG                       20

(2) INFORMATION FOR SEQ ID NO:6:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:6:

AACATACGTG GCTCTATGCA                       20

(2) INFORMATION FOR SEQ ID NO:7:

(i) SEQUENCE CHARACTERISTICS:
    (A) LENGTH: 291
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:7:

AATCTGGGCG ACAAGAGTGA AACTCCGTCA AAAGAAAGAA AGAAAGAGAC AAAGAGAGTT      60

AGAAAGAAAG AAAGAGAGAG AGAGAGAAAG GAAGGAAGGA AGAAAAAGAA AGAAAAAGAA    120

AGAAAGAGAA AGAAAGAAAG AGAAAGAAAG AAAGAAAGAA AGAAAGAAAG AAAGAAAGAA    180

AGAAAGAAAA AGAAAGAAAG AAAGAAAGAA AGAAAGAAAG AAAGAAAGAA AGAAAGAAAG    240

AAAGAAAGGA AGGAAAGAAA GAGCAAGTTA CTATAGCGGT AGGGGAGATG T             291

(2) INFORMATION FOR SEQ ID NO:8:

(i) SEQUENCE CHARACTERISTICS:

(A) LENGTH: 128
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:8:

```
GCCAGTGATG CTAAAGGTTG TATTGCATAT ATACATATAT ATATATATAT ATATATATAT      60
ATATATATAT ATATATATAT ATATATATAT TTTAATTTGA TAGTATTGTG CATAGAGCCA     120
CGTATGTT                                                              128
```

(2) INFORMATION FOR SEQ ID NO:9:

(i) SEQUENCE CHARACTERISTICS:
        (A) LENGTH: 243
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:9:

```
TCCAGCCTCG GAGACAGAAT GAGACTCCAT CAAAACAAG  AAAGAAAGAA AGACAAAGAG      60
AGAAAGAAAG AAAGAAAGAA AGAAAGAAAG AGAGAGAG   AGAGAGAGAG AGAAAGAAAG     120
AAAGAAAGAA AGAAAGAAAG AAAGAAAGAA AGAAAGAAAG AAAGAAAGAA GGAAAGAAAG     180
AAAGGAAACT AAAATAACTA AATAACTGAG TAGCACCACA CCACCTGCTC TGGAGAAAGG     240
ACT                                                                    243
```

(2) INFORMATION FOR SEQ ID NO:10:

(i) SEQUENCE CHARACTERISTICS:
        (A) LENGTH: 19
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

```
TTTCTGGGTG TGTCTGAAT                                                    19
```

(2) INFORMATION FOR SEQ ID NO:11:

(i) SEQUENCE CHARACTERISTICS:
        (A) LENGTH: 20
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:11:

```
ACACAGTTGC TCTAAAGGGT                                                   20
```

(2) INFORMATION FOR SEQ ID NO:12:

(i) SEQUENCE CHARACTERISTICS:
        (A) LENGTH: 20
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:12:

```
CTAGGTTGTA AGCTCCATGA                                                   20
```

( 2 ) INFORMATION FOR SEQ ID NO:13:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TTGAGCACTT ACTCTGTGCC                                        20

( 2 ) INFORMATION FOR SEQ ID NO:14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AACTCAGAAC AGTGCCTGAC                                        20

( 2 ) INFORMATION FOR SEQ ID NO:15:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

ATTTCCCTCA AGGCTCCAGG T                                     21

( 2 ) INFORMATION FOR SEQ ID NO:16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CTGATCTTGC TCACCTTCGA                                        20

( 2 ) INFORMATION FOR SEQ ID NO:17:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GCGTTTGCTG AAATGAAGGA                                        20

( 2 ) INFORMATION FOR SEQ ID NO:18:

( i ) SEQUENCE CHARACTERISTICS:
        ( A ) LENGTH: 20
        ( B ) TYPE: nucleic acid ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:18:

GCAGGTACTT AGTTAGCTAC                                                      20

( 2 ) INFORMATION FOR SEQ ID NO:19:

( i ) SEQUENCE CHARACTERISTICS:
            ( A ) LENGTH: 20
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:19:

TTACAGTGAG CCAAGGTCGT                                                      20

( 2 ) INFORMATION FOR SEQ ID NO:20:

( i ) SEQUENCE CHARACTERISTICS:
            ( A ) LENGTH: 20
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:20:

TTTGTCTGGA TAGACTGGAG                                                      20

( 2 ) INFORMATION FOR SEQ ID NO:21:

( i ) SEQUENCE CHARACTERISTICS:
            ( A ) LENGTH: 19
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:21:

CCATCTTCCT GTGGCTGTA                                                       19

( 2 ) INFORMATION FOR SEQ ID NO:22:

( i ) SEQUENCE CHARACTERISTICS:
            ( A ) LENGTH: 20
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:22:

CTAATGCAGA GATTTAGGGC                                                      20

( 2 ) INFORMATION FOR SEQ ID NO:23:

( i ) SEQUENCE CHARACTERISTICS:
            ( A ) LENGTH: 20
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:23:

GTGGTGTAAA GACTGCATAG                                                         20

( 2 ) INFORMATION FOR SEQ ID NO:24:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

ATGTGACTGA TGTGGGTCAG                                                         20

( 2 ) INFORMATION FOR SEQ ID NO:25:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CATCTGCACT CATGCTCCAT                                                         20

( 2 ) INFORMATION FOR SEQ ID NO:26:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TCCCAGATCG CTCTACATGA                                                         20

( 2 ) INFORMATION FOR SEQ ID NO:27:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CACAGCTTCA GAAGTCACAG                                                         20

( 2 ) INFORMATION FOR SEQ ID NO:28:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GAGCAATGTT GCTTAGGATG                                                         20

( 2 ) INFORMATION FOR SEQ ID NO:29:

( i ) SEQUENCE CHARACTERISTICS:
        ( A ) LENGTH: 20

(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:29:

TGGAAGTGTC ACTGGCATGT                      20

(2) INFORMATION FOR SEQ ID NO:30:

(i) SEQUENCE CHARACTERISTICS:
    (A) LENGTH: 21
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:30:

TGTGTCCAGC CTTAGTGTGC A                    21

(2) INFORMATION FOR SEQ ID NO:31:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:31:

TCATCACTTC CAGAATGTGC                      20

(2) INFORMATION FOR SEQ ID NO:32:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:32:

ACTGCCTCAT CCAGTTTCAG                      20

(2) INFORMATION FOR SEQ ID NO:33:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:33:

GAGCAGGCAC TTGTTAGATG                      20

(2) INFORMATION FOR SEQ ID NO:34:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:34:

CCTCTTGGCT CTAACAGCAA 20

(2) INFORMATION FOR SEQ ID NO:35:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

AGCAAGACCC TGTCTCAAGA 20

(2) INFORMATION FOR SEQ ID NO:36:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CAAGGCCCAT CTTCAGTAGA 20

(2) INFORMATION FOR SEQ ID NO:37:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CCTTCTCACT CCTTTACTAG 20

(2) INFORMATION FOR SEQ ID NO:38:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

GAAGACTGAG GAGGTCAGAA 20

(2) INFORMATION FOR SEQ ID NO:39:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

CTACTGTTCA GAGTCAAAGC 20

(2) INFORMATION FOR SEQ ID NO:40:

(i) SEQUENCE CHARACTERISTICS:

(A) LENGTH: 20
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:40:

TGCCCCACAT TAGGATGCAT 20

(2) INFORMATION FOR SEQ ID NO:41:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:41:

AGGGACACGA ATCAGATCAG 20

(2) INFORMATION FOR SEQ ID NO:42:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:42:

GTGGTACCTC ATTGTGGCTA 20

(2) INFORMATION FOR SEQ ID NO:43:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:43:

AGGCATCCTT GTGCTGACAT 20

(2) INFORMATION FOR SEQ ID NO:44:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:44:

TTTGGCCGAC AGTGGTGTAA 20

(2) INFORMATION FOR SEQ ID NO:45:

(i) SEQUENCE CHARACTERISTICS:
(A) LENGTH: 20
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:45:

AGGACCAAAC CATGTCTGTC                                        20

( 2 ) INFORMATION FOR SEQ ID NO:46:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CTGCATCTGA GCATATGGGA                                        20

( 2 ) INFORMATION FOR SEQ ID NO:47:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CATTCAGACT ATGCAGGCTT                                        20

( 2 ) INFORMATION FOR SEQ ID NO:48:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

CTGGGACTAC TGGCACATG                                         19

( 2 ) INFORMATION FOR SEQ ID NO:49:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

GGCAACGTGG TGAAACCTT                                         19

( 2 ) INFORMATION FOR SEQ ID NO:50:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

GGAAGATGGA GTGGCTGTTA                                        20

( 2 ) INFORMATION FOR SEQ ID NO:51:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CTCCAGCCTG GCGAAAGAAT                             20

( 2 ) INFORMATION FOR SEQ ID NO:52:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:52:

GTAAGACTTT TGGAGCCATT                             20

( 2 ) INFORMATION FOR SEQ ID NO:53:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:53:

TTCAGGGAGA ATGAGATGGG                             20

( 2 ) INFORMATION FOR SEQ ID NO:54:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:54:

GACAGAGTGA GACTCCATCT                             20

( 2 ) INFORMATION FOR SEQ ID NO:55:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:55:

GATCCTATCT TCTCAGGAGG                             20

( 2 ) INFORMATION FOR SEQ ID NO:56:

( i ) SEQUENCE CHARACTERISTICS:
                ( A ) LENGTH: 20
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:56:

GAGGTTGCAC TCCAGCCTTT                                                     20

( 2 ) INFORMATION FOR SEQ ID NO:57:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

ATGCCATGCA GATTAGAAA                                                      19

( 2 ) INFORMATION FOR SEQ ID NO:58:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

GGAAAGAAAC AGTGAAAGA                                                      19

( 2 ) INFORMATION FOR SEQ ID NO:59:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

ATCCATCGAC CTCTGGGTTA                                                     20

( 2 ) INFORMATION FOR SEQ ID NO:60:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

GACCCCACAG CCTATTCAGA                                                     20

( 2 ) INFORMATION FOR SEQ ID NO:61:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

TTGACTGCTG AACGGCTGCA                                                     20

( 2 ) INFORMATION FOR SEQ ID NO:62:

( i ) SEQUENCE CHARACTERISTICS:
    ( A ) LENGTH: 19
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:62:

CAGCTGCCCT AGTCAGCAC                                                                                                                  19

( 2 ) INFORMATION FOR SEQ ID NO:63:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:63:

GCTTCCGAGT GCAGGTCACA                                                                                                            20

( 2 ) INFORMATION FOR SEQ ID NO:64:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:64:

GGGCAACATG GTGAAACCTT                                                                                                             20

( 2 ) INFORMATION FOR SEQ ID NO:65:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:65:

CCTAGCCTAT ACTTCCTTTC                                                                                                             20

( 2 ) INFORMATION FOR SEQ ID NO:66:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:66:

GGACCTCGTG AATTACAATC                                                                                                       20

( 2 ) INFORMATION FOR SEQ ID NO:67:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:67:

ATTTACCTAC CTGTTCATCC                                                           20

( 2 ) INFORMATION FOR SEQ ID NO:68:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

TTGTGTCAAC TGCTGATATG                                                           20

( 2 ) INFORMATION FOR SEQ ID NO:69:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

AACCAAAACA TCATTCCCTA                                                           20

( 2 ) INFORMATION FOR SEQ ID NO:70:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

CGTAAGCGTG CACTATACCC T                                                         21

( 2 ) INFORMATION FOR SEQ ID NO:71:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

CTGAGGATTC ATCCACCTG                                                            19

( 2 ) INFORMATION FOR SEQ ID NO:72:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

CCTGAGTAGC TGTTAAGGGA                                                           20

( 2 ) INFORMATION FOR SEQ ID NO:73:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:73:

GCACATGTAC CCTAGAACTT        20

FIVE HIGHLY INFORMATIVE MICROSATELLITE REPEAT POLYMORPHIC DNA MARKERS

This is a continuation-in-part of U.S. application Ser. No. 07/799,828, filed Nov. 27, 1991, allowed which is a continuation-in-part of U.S. application Ser. No. 07/707,501, filed May 29, 1991, abandoned.

TECHNICAL FIELD

This application relates to genetic testing with polymorphic DNA markers having repeat sequences to provide a rapid and convenient high resolution process for distinguishing target nucleic acid segments on the basis of nucleotide differences according to human individualization wherein the nucleic acid segments differ in size.

BACKGROUND ART

The science of genetics has taken a keen interest in the identification of human individualization and genetic relationships between individuals. Each individual has hereditary material (DNA, "nucleotides") which is unique to that individual and hereditary material which is related to that of others. Procedures have been developed which are based on identification and characterization of changes in DNAs, which are changes in DNA (DNA polymorphisms) due to nucleotide substitution, insertion, or deletion within the chains of DNAs.

In the field of forensic medicine, for example, there is a keen interest in such polymorphisms for identification purposes. Forensic geneticist have developed many techniques to compare homologous segments of DNA to determine if the segments are identical or if they differ in one or more nucleotides. Practical applications of these techniques relate to fields other than forensic medicine, for example, genetic disease diagnosis and human genome mapping.

At the present time in this art, the most accurate and informative way to compare DNA segments requires a method which provides the complete nucleotide sequence for each DNA segment. Particular techniques have been developed for determining actual sequences in order to study mutation in human genes. See, for example, Proc. Natl. Acad. Sci. U.S.A. 85, 544–548 (1988) and Nature 330, 384–386 (1987). However, because of the extensive amounts of time and high costs to determine, interpret, and compare sequence information, presently it is not practical to use extensive sequencing for compare more than just a few DNA segments.

In genetic mapping, the most frequently used screening for DNA polymorphisms arising from mutations consist of digesting the DNA strand with restriction endonucleases and analyzing the resulting fragments by means of Southern blots. See Am. J. Hum. Genet. 32, 314–331 (1980) or Sci. Am. 258, 40–48 (1988). Since mutations often occur randomly they may affect the recognition sequence of the endonuclease and preclude the enzymatic cleavage at that cite. Restriction fragment length polymorphism mappings (RFLPS) are based on changes at the restriction site. They are accurate but not very informative (PIC [0.3). The major problem with RFLPs is the inability of a test to detect changes that do not affect cleavage with a restriction endonuclease. As in many of the test methods in the DNA art, the methods used to detect RFLPs are very labor intensive and expensive, especially the techniques which includes Southern blot analysis.

Another technique for detecting specific mutations in particular DNA segment involves hybridizing DNA segments which are being analyzed (target DNA) with a complimentary, labeled oligonucleotide probe. See Nucl. Acids Res. 9, 879–894 (1981). Since DNA duplexes containing even a single base pair mismatch exhibit high thermal instability, the differential melting temperature can be used to distinguish target DNAs that are perfectly complimentary to the probe from target DNAs that only differ by a single nucleotide. This method has been adapted to detect the presence or absence of a specific restriction site, U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Another process for studying differences in DNA structure is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product.

Another process exploits the fact that the incorporation of some nucleotide analogs into DNA causes an incremental shift of mobility when the DNA is subjected to a size fractionation process, such as electrophoresis. Nucleotide analogs can be used to identify changes since they can cause an electrophoretic mobility shift. See, U.S. Pat. No. 4,879,214.

Unfortunately, the above techniques used for identification of polymorphisms are either not very informative or take a long period of time to perform. For example, techniques which identify changes in individual nucleotides on a particular DNA strand often take at least three to four days to perform. Accordingly, such tests are very labor intensive and expensive to perform.

Further, subtle genetic differences among related individuals regarding nucleotides which are substituted in the DNA chains are difficult to detect. VNTR's or Jeffrey's probes (which the FBI is using to test and identify DNA chains) are very informative but labor intensive, in distinction to microsatellites as our which are equally informative PCR based polymormismic.

The use of certain nucleotide repeat polymorphisms for identifying or comparing DNA segments have been described by Weber & May 89 Am Hum Genet 44:388, Litt & Luthy '89 Am) Hum Genet 44:397). However the particular polymorphism genetic segments and primers used to identify the polymorphisms (for identification and comparison purposes) of the present invention have not been previously known or suspected.

Accordingly, there a need in this art for a rapid, simple, inexpensive and accurate technique having a very high resolution value to determine relationships between individuals and differences in degree of relationships. Also, there is a need in the art for a very accurate genetic relationship test procedure which uses very small amounts of an original DNA sample, yet produces very accurate results. This is particularly true in the forensic medicine area and criminology, since often times very small samples of DNA are available for testing.

DISCLOSURE OF THE INVENTION

An object of the present invention is to provide a fast and accurate test for measuring the subtle differences in individuals by way of genetic testing.

Another object of the invention relates to polymorphic markers that can be used for human individualization.

A further object of the invention is to provide a fast and accurate technique for measuring the subtle differences in individuals by way of genetic testing that can be applied in multiple areas, e.g., forensic screening, paternity and prenatal screening and genetic mapping.

A still further object is to provide an improved method for conducting a PCR procedure using an effective amount of a nucleotide according to the present invention and to provide an PCR assay kit comprising an effective amount of a nucleotide according to the present invention and ancillary PCR reagents.

BRIEF DESCRIPTION OF DRAWINGS

FIG. 1 relates to a nucleotide sequence according to SEQ ID NO:1.

FIG. 2 relates to a nucleotide sequence according to SEQ ID NO:2.

FIG. 3 relates to a nucleotide sequence according to SEQ ID NO:3.

FIG. 4 relates to a nucleotide sequence according to SEQ ID NO:4.

FIG. 5 relates to a nucleotide sequence according to SEQ ID NO:5.

FIG. 6 relates to a nucleotide sequence according to SEQ ID NO:6.

FIG. 7 relates to a nucleotide sequence according to SEQ ID NO:7.

FIG. 8 relates to a nucleotide sequence according to SEQ ID NO:8.

FIG. 9 relates to a nucleotide sequence according to SEQ ID NO:9.

FIG. 10 relates to a nucleotide sequence according to SEQ ID NO:10.

FIG. 11 relates to a nucleotide sequence according to SEQ ID NO:11.

FIG. 12 relates to a nucleotide sequence according to SEQ ID NO:12.

FIG. 13 relates to a nucleotide sequence according to SEQ ID NO:13.

FIG. 14 relates to a nucleotide sequence according to SEQ ID NO:14.

FIG. 15 relates to a nucleotide sequence according to SEQ ID NO:15.

FIG. 16 relates to a nucleotide sequence according to SEQ ID NO:16.

FIG. 17 relates to a nucleotide sequence according to SEQ ID NO:17.

FIG. 18 relates to a nucleotide sequence according to SEQ ID NO:18.

FIG. 19 relates to a nucleotide sequence according to SEQ ID NO:19.

FIG. 20 relates to a nucleotide sequence according to SEQ ID NO:20.

FIG. 21 relates to a nucleotide sequence according to SEQ ID NO:21.

FIG. 22 relates to a nucleotide sequence according to SEQ ID NO:22.

FIG. 23 relates to a nucleotide sequence according to SEQ ID NO:23.

FIG. 24 relates to a nucleotide sequence according to SEQ ID NO:24.

FIG. 25 relates to a nucleotide sequence according to SEQ ID NO:25.

FIG. 26 relates to a nucleotide sequence according to SEQ ID NO:26.

FIG. 27 relates to a nucleotide sequence according to SEQ ID NO:27.

FIG. 28 relates to a nucleotide sequence according to SEQ ID NO:28.

FIG. 29 relates to a nucleotide sequence according to SEQ ID NO:29.

FIG. 30 relates to a nucleotide sequence according to SEQ ID NO:30.

FIG. 31 relates to a nucleotide sequence according to SEQ ID NO:31.

FIG. 32 relates to a nucleotide sequence according to SEQ ID NO:32.

FIG. 33 relates to a nucleotide sequence according to SEQ ID NO:33.

FIG. 34 relates to a nucleotide sequence according to SEQ ID NO:34.

FIG. 35 relates to a nucleotide sequence according to SEQ ID NO:35.

FIG. 36 relates to a nucleotide sequence according to SEQ ID NO:36.

FIG. 37 relates to a nucleotide sequence according to SEQ ID NO:37.

FIG. 38 relates to a nucleotide sequence according to SEQ ID NO:38.

FIG. 39 relates to a nucleotide sequence according to SEQ ID NO:39.

FIG. 40 relates to a nucleotide sequence according to SEQ ID NO:40.

FIG. 41 relates to a nucleotide sequence according to SEQ ID NO:41.

FIG. 42 relates to a nucleotide sequence according to SEQ ID NO:42.

FIG. 43 relates to a nucleotide sequence according to SEQ ID NO:43.

FIG. 44 relates to a nucleotide sequence according to SEQ ID NO:44.

FIG. 45 relates to a nucleotide sequence according to SEQ ID NO:45.

FIG. 46 relates to a nucleotide sequence according to SEQ ID NO:46.

FIG. 47 relates to a nucleotide sequence according to SEQ ID NO:47.

FIG. 48 relates to a nucleotide sequence according to SEQ ID NO:48.

FIG. 49 relates to a nucleotide sequence according to SEQ ID NO:49.

FIG. 50 relates to a nucleotide sequence according to SEQ ID NO:50.

FIG. 51 relates to a nucleotide sequence according to SEQ ID NO:51.

FIG. 52 relates to a nucleotide sequence according to SEQ ID NO:52.

FIG. 53 relates to a nucleotide sequence according to SEQ ID NO:53.

FIG. 54 relates to a nucleotide sequence according to SEQ ID NO:54.

FIG. 55 relates to a nucleotide sequence according to SEQ ID NO:55.

FIG. 56 relates to a nucleotide sequence according to SEQ ID NO:56.

FIG. 57 relates to a nucleotide sequence according to SEQ ID NO:57.

FIG. 58 relates to a nucleotide sequence according to SEQ ID NO:58.

FIG. 59 relates to a nucleotide sequence according to SEQ ID NO:59.

FIG. 60 relates to a nucleotide sequence according to SEQ ID NO:60.

FIG. 61 relates to a nucleotide sequence according to SEQ ID NO:61.

FIG. 62 relates to a nucleotide sequence according to SEQ ID NO:62.

FIG. 63 relates to a nucleotide sequence according to SEQ ID NO:63.

FIG. 64 relates to a nucleotide sequence according to SEQ ID NO:64.

FIG. 65 relates to a nucleotide sequence according to SEQ ID NO:65.

FIG. 66 relates to a nucleotide sequence according to SEQ ID NO:66.

FIG. 67 relates to a nucleotide sequence according to SEQ ID NO:67.

FIG. 68 relates to a nucleotide sequence according to SEQ ID NO:68.

FIG. 69 relates to a nucleotide sequence according to SEQ ID NO:69.

FIG. 70 relates to a nucleotide sequence according to SEQ ID NO:70.

FIG. 71 relates to a nucleotide sequence according to SEQ ID NO:71.

FIG. 72 related to a nucleotide sequence according to SEQ ID NO:72.

FIG. 73 related to a nucleotide sequence according to SEQ ID NO:73.

BEST MODE FOR CARRYING OUT THE INVENTION

The present invention provides a fast and accurate test for measuring subtle genetic differences in individuals by way of genetic testing. The invention further relates to polymorphic markers (two tetranucleotide and one dinucleotide repeat polymorphisms) that can be used for human individualization. The invention further relates to twenty-seven other polymorphic markers useful for human individualization. The invention still further relates to five other polymorphic markers and the five primer pairs useful for measuring the subtle genetic differences relating to the five polymorphic markers. Applications for the technique and markers according to the invention are for example, in forensic screening, in paternity and prenatal screening as well as in genetic mapping.

The invention relates to polymorphic markers (two tetranucleotide, one dinucleotide repeat polymorphisms, twenty-seven other unique polymorphic markers, and five more unique polymorphic markers) that are useful for human individualization for a forensic screen, and for paternity and prenatal screening as well as genetic mapping. The markers according to the present invention have high polymorphism information content (PIC) values. The first three markers are characterized by sets of oligonucleotide primers as follows:

1. Set 1, PIC 0.92
   a. A nucleotide sequence according to SEQ ID NO:1
   b. A nucleotide sequence according to SEQ ID NO:2
2. Set 2, PIC 0.91
   a. A nucleotide sequence according to SEQ ID NO:3
   b. A nucleotide sequence according to SEQ ID NO:4
3. Set 3, PIC 0.92
   a. A nucleotide sequence according to SEQ ID NO:5
   b. A nucleotide sequence according to SEQ ID NO:6.

These polymorphic markers (two tetranucleotide and one dinucleotide repeat polymorphisms which are also accompanied by beginning and ending nucleotide sequences) that can be used for human individualization are further characterized by the following marker sequences.

1. A nucleotide sequence having a repeat polymorphism according to SEQ ID NO:7.
2. A nucleotide sequence having a repeat polymorphism according to SEQ ID NO:8.
3. A nucleotide sequence having a repeat polymorphism according to SEQ ID NO:9.

Since a polymorphic marker and an index locus occur as a "pair", attaching a primer oligonucteotide according to the present invention to the polymorphic marker allows PCR amplification of the segment pair. The amplified DNA segment can then be resolved by electrophoresis and autoradiography. A resulting autoradiography can then be analyzed for its similarity to another DNA segment autoradiography. Following the PCR amplification procedure, electrophoretic motility enhancing DNA analogs may optionally be used to increase the accuracy of the electrophoresis step.

Twenty-seven other primary pair sequences for detecting unique polymorphisms are sequences according to SEQ ID NO:10 through SEQ ID NO:63. Additionally, five other primary pair sequences for detecting unique polymorphisms are sequences according to SEQ ID NO:64 through SEQ ID NO:73.

The described polymorphisms are useful for human sample individualization, because of their high PIC values. Since the described polymorphisms are based on the polymerase chain reaction, only minute amounts of genomic DNA are required for each test. The target sequences range from 69–260 bps in length so that high molecular weight DNA is not necessary and common problems such as shearing of DNA will have minimal impact on the performance of the assay. The assay is easy to perform and results can be obtained within 24 hours. Microsatellite repeat polymorphisms have been shown to be useful tools in DNA analysis. The 27 polymorphisms described here are original and are based on previously sequenced human genes. The five further polymorphisms described are original. The most commonly used technique in forensic screening is based on minisatellite markers in distinction to the PCR able microsatellites described here.

The 27 markers are characterized by sets of oligonucleotide primers as set forth in Table 1, below. The 27 pairs are indicated in Table 1 as 1A–27A, respectively. Also indicated is the locus, the chromosomal location, the primer SEQ ID NO:, the degree of heterozygousness, the PIC value, the size, the repeat sequence and the number of alleles.

The additional five markers are characterized by sets of oligonucleotide primers as set forth in Table 2, below. These five pairs are indicated in Table 2 as 1B–5B, respectively. Also indicated is the locus, the chromosomal location, the primer SEQ ID NO:, the degree of heterozygousness, the PIC value, the size, the repeat sequence and the number of alleles.

TABLE 1

| Pair # | Locus | Chromosomal Location | Primer SEQ ID NO: | Heteroz | PIC | Size | Repeat | No. of alleles |
|---|---|---|---|---|---|---|---|---|
| 1A | Int-2 | 11q13 | 10,11 | 84.6% | 0.79 | 161–177 | $(TG)_5TC(TG)_{16}$ | 9 |
| 2A | PLA-AZ | 12 | 12,13 | 73.3% | 0.76 | 122–137 | $(TTA)_{16}$ | 6 |
| 3A | FABP2 | 4q28–31 | 14,15 | 64% | 0.64 | 99–117 | $(TTA)_{13}$ | 6 |
| 4A | THRO01 | 15q15 | 16,17 | 60% | 0.58 | 165–181 | $(CT)_{14}$ | 9 |
| 5A | CYARP450 | 15Fq21.1 | 18,19 | 91.3% | 0.67 | 175–199 | $(TTTA)_8$ | 5 |
| 6A | GCG | 2q36–q37 | 20,21 | 88% | 0.77 | 142–172 | $(GA)_{19}$ | 11 |
| 7A | IL-9 | 5q | 22,23 | 62.5% | 0.75 | 127–139 | $(TG)_{20}$ | 7 |
| 8A | CSTP1 | 20 | 24,25 | 61% | 0.58 | 123–141 | $(GT)_{15}$ |  |
| 9A | ANKYRIN | 8p11.1–21.1 | 26,27 | 54% | 0.45 | 107–113 | $(AC)_{14}$ | 4 |
| 10A | CD-19 | 16 | 28,29 | 40% | 0.39 | 79–91 | $(GT)_{17}$ | 7 |
| 11A | c-fms | 5q33.3–34 | 30,31 | 86% | 0.85 | 95–127 | $(GT)_{26}$ | 10 |
| 12A | CD 8 | 2p12 | 32,33 | 71% | 0.66 | 138–170 | $(AC)_{14}$ | 7 |
| 13A | CYP2D7-8 | 22 | 34,35 | 80% | 0.78 | 98–116 | $(GT)_{18}$ | 10 |
| 14A | W 30 | 7q | 36,37 | 74% | 0.72 |  |  | 11 |
| 15A | HMG-14 | 21 | 38,39 | 69% | 0.67 | 69–93 | $(GT)_{19}$ | 10 |
| 16A | RHO | 3 | 40,41 | 72% | 0.68 | 145–169 |  | 5 |
| 17A | PFKL | 21q22.3 | 42,43 | 70% | 0.66 | 129–145 | $(AC)_{16}$ | 7 |
| 18A | HSFLT | 13q12 | 44,45 | 51% | 0.49 | 164–186 | $(TG)_{21}$ | 8 |
| 19A | HSMYHO1 | 14 | 46,47 | 66% | 0.60 | 90–102 | $(GT)_{15}$ | 6 |
| 20A | HSATPSY1 | 12p13-qter | 48,49 | 60% | 0.54 | 111–117 | $(GT)_{11}$ | 4 |
| 21A | CFES PPS | 15q25-qter | 50,51 | 75% | 0.70 | 143–163 | $(ATTT)_{11}$ | 6 |
| 22A | DHFRP2 | 6 | 52,53 | 70% | 0.66 | 157–173 | $(AAAC)_7$ | 5 |
| 23A | CRYG1 | 2q34–35 | 54,55 | 68% | 0.61 | 117–126 | $(AAC)_9$ | 4 |
| 24A | F13A1 | 6p24–25 | 56,57 | 78% | 0.75 | 180–230 | $(AAAG)_7$ | 8 |
| 25A | TRM1 | 6p23–q12 | 58,59 | 54% | 0.50 | 174–186 | $(AAC)_8$ | 5 |
| 26A | II-D | 6 | 60,61 | 81% | 0.78 | 185–206 | $(CAG)_{18}$ | 7 |
| 27A | TH | 11p15.5–p15 | 62,63 | 78% | 0.75 | 244–260 | $(TCAT)_9$ | 5 |

TABLE 2

| Pair # | Locus | Chromosomal Location | Primer SEQ ID NO: | Heteroz | PIC | Size | Repeat | No. of alleles |
|---|---|---|---|---|---|---|---|---|
| 1B | ACPP | 3q21-qter | 64 | 69 | 0.65 | 260–280 | $(AAAT)_{11}$ | 6 |
|  |  |  | 65 |  |  |  |  |  |
| 2B | MSP | 18q23-qter | 66 | 80% | 0.77 | 208–232 | $(ATGG)_{12}, (TGGA)_9$ | 7 |
|  |  |  | 67 | 79% | 0.76 | 122–142 | $(ATGG)_{12}$ | 6 |
| 3B | IGF1 | 12q23 | 68 | 53% | 0.52 | 173–207 | $(CT)_{16}$ | 11 |
| 4B | GABRB1 | 4p12–p13 | 70 | 72% | 0.68 | 91–99 | $(AC)_{19}$ | 5 |
| 5B | MYC | 8q24 | 72 | 86% | 0.85 | 87–125 | $(AT)_{23}$ | 15 |
|  |  |  | 73 |  |  |  |  |  |

Also, the invention relates to a method for conducting a PCR procedure comprising using an effective amount of at least one nucleotide according to according to the invention as set forth above, wherein the nucleotide is part of a primer pair of nucleotides selected from the group of nucleotide pairs consisting of a) a polynucleotide having the sequence as set forth in SEQ ID NO:1 and a polynucleotide having a sequence as set forth in SEQ ID NO:2;

b) a polynucleotide having the sequence as set forth in SEQ ID NO:3 and a polynucleotide having the sequence as set forth in SEQ ID NO:4;

c) a polynucleotide having the sequence as set forth in SEQ ID NO:5 and a polynucleotide having the sequence as set forth in SEQ ID NO:6;

d) a polynucleotide having the sequence as set forth in SEQ ID NO:10 and a polynucleotide having the sequence as set forth in SEQ ID NO:11;

e) a polynucleotide having the sequence as set forth in SEQ ID NO:12 and a polynucleotide having the sequence as set forth in SEQ ID NO:13;

f) a polynucleotide having the sequence as set forth in SEQ ID NO:14 and a polynucleotide having the sequence as set forth in SEQ ID NO:15;

g) a polynucleotide having the sequence as set forth in SEQ ID NO:16 and a polynucleotide having the sequence as set forth in SEQ ID NO:17;

h) a polynucleotide having the sequence as set forth in SEQ ID NO:18 and a polynucleotide having the sequence as set forth in SEQ ID NO:19;

i) a polynucleotide having the sequence as set forth in SEQ ID NO:20 and a polynucleotide having the sequence as set forth in SEQ ID NO:21;

j) a polynucleotide having the sequence as set forth in SEQ ID NO:22 and a polynucleotide having the sequence as set forth in SEQ ID NO:23;

k) a polynucleotide having the sequence as set forth in SEQ ID NO:24 and a polynucleotide having the sequence as set forth in SEQ ID NO:25;

l) a polynucleotide having the sequence as set forth in SEQ ID NO:26 and a polynucleotide having the sequence as set forth in SEQ ID NO:27;

m) a polynucleotide having the sequence as set forth in SEQ ID NO:28 and a polynucleotide having the sequence as set forth in SEQ ID NO:29;

n) a polynucleotide having the sequence as set forth in SEQ ID NO:30 and a polynucleotide having the sequence as set forth in SEQ ID NO:31;

o) a polynucleotide having the sequence as set forth in SEQ ID NO:32 and a polynucleotide having the sequence as set forth in SEQ ID NO:33;

p) a polynucleotide having the sequence as set forth in SEQ ID NO:34 and a polynucleotide having the sequence as set forth in SEQ ID NO:35;

q) a polynucleotide having the sequence as set forth in SEQ ID NO:36 and a polynucleotide having the sequence as set forth in SEQ ID NO:37;

r) a polynucleotide having the sequence as set forth in SEQ ID NO:38 and a polynucleotide having the sequence as set forth in SEQ ID NO:39;

s) a polynucleotide having the sequence as set forth in SEQ ID NO:40 and a polynucleotide having the sequence as set forth in SEQ ID NO:41;

t) a polynucleotide having the sequence as set forth in SEQ ID NO:42 and a polynucleotide having the sequence as set forth in SEQ ID NO:43;

u) a polynucleotide having the sequence as set forth in SEQ ID NO:44 and a polynucleotide having the sequence as set forth in SEQ ID NO:45;

v) a polynucleotide having the sequence as set forth in SEQ ID NO:46 and a polynucleotide having the sequence as set forth in SEQ ID NO:47;

w) a polynucleotide having the sequence as set forth in SEQ ID NO:48 and a polynucleotide having the sequence as set forth in SEQ ID NO:49;

x) a polynucleotide having the sequence as set forth in SEQ ID NO:50 and a polynucleotide having the sequence as set forth in SEQ ID NO:51;

y) a polynucleotide having the sequence as set forth in SEQ ID NO:52 and a polynucleotide having the sequence as set forth in SEQ ID NO:53;

z) a polynucleotide having the sequence as set forth in SEQ ID NO:54 and a polynucleotide having the sequence as set forth in SEQ ID NO:55;

aa) a polynucleotide having the sequence as set forth in SEQ ID NO:56 and a polynucleotide having the sequence as set forth in SEQ ID NO:57;

bb) a polynucleotide having the sequence as set forth in SEQ ID NO:58 and a polynucleotide having the sequence as set forth in SEQ ID NO:59;

cc) a polynucleotide sequence having the sequence as set forth in SEQ ID NO:60 and a polynucleotide sequence as set forth in SEQ ID NO:61;

dd) a polynucleotide having the sequence as set forth in SEQ ID NO:62 and a polynucleotide having the sequence as set forth in SEQ ID NO:63.

ee) a polynucleotide having the sequence as set forth in SEQ ID NO:64 and a polynucleotide having the sequence as set forth in SEQ ID NO:65;

ff) a polynucleotide having the sequence as set forth in SEQ ID NO:66 and a polynucleotide having the sequence as set forth in SEQ ID NO:67;

gg) a polynucleotide having the sequence as set forth in SEQ ID NO:68 and a polynucleotide having the sequence as set forth in SEQ ID NO:69;

hh) a polynucleotide having the sequence as set forth in SEQ ID NO:70 and a polynucleotide having the sequence as set forth in SEQ ID NO:71;

ii) a polynucleotide having the sequence as set forth in SEQ ID NO:72 and a polynucleotide having the sequence as set forth in SEQ ID NO:73.

Therefore, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according no SEQ ID NO:8 and a sequence according to SEQ ID NO:9, which comprises a. obtaining nucleotide segments comprising said repeat polymorphisms in an amount effective for testing, b. amplifying said segments by a PCR procedure using a pair of oligonucleotide primers capable of amplifying said polymorphism containing segments, c. resolving the amplified segments using page gels electrophoresis, and d. comparing the resolved segments by autoradiography to observe the differences in migration patterns due to length variation.

Preferably, the invention further relates to an assay for measuring the subtle differences in genetic material regarding an added or omitted set of dinucleotide or tetranucleotide repeat polymorphisms selected from the group consisting of a sequence according to SEQ ID NO:7, a sequence according to SEQ ID NO:8 and a sequence according to SEQ ID NO:9, which comprises a. obtaining nucleotide segments comprising said repeat polymorphisms in an amount effective for testing, b. amplifying said segments by a PCR procedure using the pair of oligonucleotide primers selected from the group consisting of a sequence according to SEQ ID NO:1, a sequence according to SEQ ID NO:2, a sequence according to SEQ ID NO:3, a sequence according to SEQ ID NO:4, a sequence according to SEQ ID NO:5, or a sequence according to SEQ ID NO:6, c. resolving the amplified segments using PAGE gels and electrophoresis, and d. comparing the resolved segments by autoradiography to observe the differences in migration patterns due to length variation.

Still further, the invention relates to an assay kit for conducting a PCR procedure comprising an effective amount of at least one nucleotide having a sequence according to the invention as set forth above, wherein the nucleotide is part of a primer pair of polynucleotides selected from the group of polynucleotide pairs consisting of a) a polynucleotide having the sequence as set forth in SEQ ID NO:1 and a polynucleotide having the sequence as set forth in SEQ ID NO:2;

b) a polynucleotide having the sequence as set forth in SEQ ID NO:3 and a polynucleotide having the sequence as set forth in SEQ ID NO:4;

c) a polynucleotide having the sequence as set forth in SEQ ID NO:5 and a polynucleotide having the sequence as set forth in SEQ ID NO:6, d) a polynucleotide having the sequence as set forth in SEQ ID NO:10 and a polynucleotide having the sequence as set forth in SEQ ID NO:11;

e) a polynucleotide having the sequence as set forth in SEQ ID NO:12 and a polynucleotide having the sequence as set forth in SEQ ID NO:13;

f) a polynucleotide having the sequence as set forth in SEQ ID NO:14 and a polynucleotide having the sequence as set forth in SEQ ID NO:15;

g) a polynucleotide having the sequence as set forth in SEQ ID NO:16 and a polynucleotide having the sequence as set forth in SEQ ID NO:17;

h) a polynucleotide having the sequence as set forth in SEQ ID NO:18 and a polynucleotide having the sequence as set forth in SEQ ID NO:19;

i) a polynucleotide having the sequence as set forth in SEQ ID NO:20 and a polynucleotide having the sequence as set forth in SEQ ID NO:21;

j) a polynucleotide having the sequence as set forth in SEQ ID NO:22 and a polynucleotide having the sequence as set forth in SEQ ID NO:23;

k) a polynucleotide having the sequence as set forth in SEQ ID NO:24 and a polynucleotide having the sequence as set forth in SEQ ID NO:25;

l) a polynucleotide having the sequence as set forth in SEQ ID NO:26 and a polynucleotide having the sequence as set forth in SEQ ID NO:27;

m) a polynucleotide having the sequence as set forth in SEQ ID NO:28 and a polynucleotide having the sequence as set forth in SEQ ID NO:29;

n) a polynucleotide having the sequence as set forth in SEQ ID NO:30 and a polynucleotide having the sequence as set forth in SEQ ID NO:31;

o) a polynucleotide having the sequence as set forth in SEQ ID NO:32 and a polynucleotide having the sequence as set forth in SEQ ID NO:33;

p) a polynucleotide having the sequence as set forth in SEQ ID NO:34 and a polynucleotide having the sequence as set forth in SEQ ID NO:35;

q) a polynucleotide having the sequence as set forth in SEQ ID NO:36 and a polynucleotide having the sequence as set forth in SEQ ID NO:37;

r) a polynucleotide having the sequence as set forth in SEQ ID NO:38 and a polynucleotide having the sequence as set forth in SEQ ID NO:39;

s) a polynucleotide having the sequence as set forth in SEQ ID NO:40 and a polynucleotide having the sequence as set forth in SEQ ID NO:41;

t) a polynucleotide having the sequence as set forth in SEQ ID NO:42 and a polynucleotide having the sequence as set forth in SEQ ID NO:43;

u) a polynucleotide having the sequence as set forth in SEQ ID NO:44 and a polynucleotide having the sequence as set forth in SEQ ID NO:45;

v) a polynucleotide having the sequence as set forth in SEQ ID NO:46 and a polynucleotide having the sequence as set forth in SEQ ID NO:47;

w) a polynucleotide having the sequence as set forth in SEQ ID NO:48 and a polynucleotide having the sequence as set forth in SEQ ID NO:49;

x) a polynucleotide having the sequence as set forth in SEQ ID NO:50 and a polynucleotide having the sequence as set forth in SEQ ID NO:51;

y) a polynucleotide having the sequence as set forth in SEQ ID NO:52 and a polynucleotide having the sequence as set forth in SEQ ID NO:53;

z) a polynucleotide having the sequence as set forth in SEQ ID NO:54 and a polynucleotide having the sequence as set forth in SEQ ID NO:55;

aa) a polynucleotide having the sequence as set forth in SEQ ID NO:56 and a polynucleotide having the sequence as set forth in SEQ ID NO:57;

bb) a polynucleotide having the sequence as set forth in SEQ ID NO:58 and a polynucleotide having the sequence as set forth in SEQ ID NO:59;

cc) a polynucleotide having the sequence as set forth in SEQ ID NO:60 and a polynucleotide having the sequence as set forth in SEQ ID NO:61;

dd) a polynucleotide having the sequence as set forth in SEQ ID NO:62 and a polynucleotide having the sequence as set forth in SEQ ID NO:63;

ee) a polynucleotide having the sequence as set forth in SEQ ID NO:64 and a polynucleotide having the sequence as set forth in SEQ ID NO:65;

ff) a polynucleotide having the sequence as set forth in SEQ ID NO:66 and a polynucleotide having the sequence as set forth in SEQ ID NO:67;

gg) a polynucleotide having the sequence as set forth in SEQ ID NO:68 and a polynucleotide having the sequence as set forth in SEQ ID NO:69;

hh) a polynucleotide having the sequence as set forth in SEQ ID NO:70 and a polynucleotide having the sequence as set forth in SEQ ID NO:71; and ii) a polynucleotide having the sequence as set forth in SEQ ID NO:72 and a polynucleotide having the sequence as set forth in SEQ ID NO:73;

wherein said polynucleotide is in combination with an effective amount of ancillary PCR reagents.

Accordingly, the above described polymorphisms are useful for human sample individualization, because of their high PIC values. Since the described polymorphic systems are based on the polymerase chain reaction (PCR), only minute (40 nanograms) amounts of genomic DNA are required for each test. The target sequences range from 92 to 310 base pairs so that high molecular weight DNA is not necessary, and common problems such as shearing of DNA will have minimal impact on the performance of the assay. The assay is easy to perform and results can be obtained within 24 hours. It is not uncommon for results to be available within 3–4 hours. By comparison, the prior art methods require a number of days before results are available, usually 3–4 days are required.

Also, the polymorphism corresponding to 1A–27A as described above and characterizes by their 27 primer pairs according to SEQ ID NO:10-SEQ NO:63 are useful for human sample individualization evaluation because of their high PIC values. Additionally, the polymorphisms corresponding to 1B–5B as described above and characterizes by their five primer pairs according to SEQ ID NO:64-SEQ ID NO:73 are useful for human sample individualization evaluation because of their high PIC values.

Further, the assay according to the invention is able to detect very small differences in nucleotide sequences. A single omission or addition of the repeat sequence will change the mobility due to the electrical nature and molecular weight of the target nucleotide sequence. These differences are clearly visible on the autoradiographs after electrophoresis.

Microsatellite repeat polymorphisms have been shown to be useful tools in DNA analysis. The three polymorphisms described here are original and are based on previously sequenced genes. The two tetranucleotide repeat markers described, can be scored easily since allele sizes differ by four base pairs. The most commonly used technique used in forensic screening is based on minisatellite markers, in distinction to the PCR able microsatellites described in the present invention.

The general PCR technique step is conducted generally as described in U.S. Pat. No. 4,683,195 to Mullis et al and U.S. Pat. No. 4,683,202 to Mullis et al, which are hereby incorporated by reference thereto. Further, electrical motility enhancing DNA analogs can optionally be used during the replication and amplification PCR procedure.

The degree of polymorphism in the genetic segments according to the present invention, which polymorphisms yield highly informative identification test results, is surprising and unexpected. The high PIC value (approximately 0.9) is totally unexpected.

Accordingly, the use of a PCR procedure and PCR primers pairs, such as those primer sequences according to SEQ ID NO:1 to SEQ ID NO:6, to detect the polymorphism DNA segment according to the present invention yields excellent results. Further use of primer sequences corresponding to SEQ ID NO:10 through SEQ ID NO:63 or SEQ ID NO:64 through SEQ ID NO:73 to detect the polymorphism yields excellent results. Such results are sufficiently accurate and informative to accurately identify DNA segments and determine degrees of relationship between DNA segments of individuals.

Moreover, conducting three sets of PCR procedures on the same DNA segment samples while using a different PCR primer pair according to the present invention for each of the three procedures yields extraordinarily accurate and informative test results. Comparison of the three sets of test results data provides extremely accurate DNA segment identification.

The following examples are provided to more specifically describe the invention which is not limited to the following examples.

The described oligonucleotide primers are used to amplify the target sequences using PCR, under the following conditions:

EXAMPLE 1

The samples are of DNA are prepared as follows.

60 ng of genomic DNA are used as template for PCR with 80 ng of each oligonucleotide primer, 0.6 units of Taq Polymerase 50 mM KCL, 10 mM Tris (pH 8.3), 1.5 mM $MgCl_2$, 0.01% gelatin, 200 uM of each dGTP, dATP, dTTP, 2.5 uM dCTP and 10 microcuries of alpha P32 dCTP., in a final reaction volume of 15 microliters. The samples are overlaid with 15 microliters of mineral oil to prevent evaporation.

EXAMPLE 2

PCR is performed for each of the samples and primers described in Example 1, above.

PCR is performed in a Techne MW-1 microplate thermocycler under the following conditions denaturation of 94 degrees C. for 1.4 min., annealing at 55 degrees C. for 2 min., and extension at 72 degrees C. for 2 min. The cycle is repeated 30 times with a final extension at 72 degrees C. for 10 min.

EXAMPLE 3

The amplified DNA segments from each of the samples described in Example 2 above are resolved by electrophoresis as follows.

Two microliters of each PCR reaction mixture sample are electrophoresed on a 6% PAGE sequencing gel and visualized by autoradiography. Exposure times for the autoradiography range from 3–16 hours.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of a disclosed embodiment. It is to be understood that the phraseology or terminology employed herein is for the purposes of description only and not of limitation.

We claim:

1. A polynucleotide selected from the group consisting of polynucleotides having a sequence according to SEQ ID NO:64 through SEQ ID NO:73.

2. A method for conducting a polymerase chain reaction procedure to detect an added or omitted set of dinucleotide or tetranucleotide repeat polymorphisms, comprising (A) obtaining a polynucleotide sample in an amount effective for testing;

(B) using an effective amount of at least one polynucleotide according to claim 1, wherein the polynucleotide is part of a pair of polynucleotide primers selected from the group consisting of a) a sequence as set forth in SEQ ID NO:64 and a sequence as set forth in SEQ ID NO:65;

b) a sequence as set forth in SEQ ID NO:66 and a sequence as set forth in SEQ ID NO:67;

c) a sequence as set forth in SEQ ID NO:68 and a sequence as set forth in SEQ ID NO:69;

d) a sequence as set forth in SEQ ID NO:70 and a sequence as set forth in SEQ ID NO:71; and e) a sequence as set forth in SEQ ID NO:72 and a sequence as set forth in SEQ ID NO:73; and (C) amplifying said sample by said polymerase chain reaction procedure using said pair of polynucleotide primers capable of amplifying said sample and detecting said polymorphisms.

3. An assay for measuring the subtle differences in genetic material regarding an added or omitted set of dinucleotide or tetranucleotide repeat polymorphisms wherein said genetic material comprises a sequence characterized by a pair of oligonucleotide primers selected from the group consisting of sequence ID NOs: 64–73, which comprises a. obtaining polynucleotide segments comprising said repeat polymorphisms in an amount effective for testing, b. amplifying said segments by a polymerase chain reaction procedure using a pair of oligonucleotide primers of claim 2 capable of amplifying said polymorphism containing segments, c. resolving the amplified segments using polyacrylamide gel electrophoresis, and d. comparing the resolved segments by autoradiography to observe the differences in migration patterns due to length variation.

4. An assay kit for conducting a polymerase chain reaction procedure comprising an effective amount of at least one polynucleotide having a sequence according to claim 1, wherein the polynucleotide is part of a pair of polynucleotide primers selected from the group consisting of a) a sequence as set forth in SEQ ID NO:64 and a sequence as set forth in SEQ ID NO:65;

b) a sequence as set forth in SEQ ID NO:66 and a sequence as set forth in SEQ ID NO:67;

c) a sequence as set forth in SEQ ID NO:68 and a sequence as set forth in SEQ ID NO:69;

d) a sequence as set forth in SEQ ID NO:70 and a sequence as set forth in SEQ ID NO:71; and e) a sequence as set forth in SEQ ID NO:72 and a sequence as set forth in SEQ ID NO:73;

wherein said effective amount of said polynucleotide is in combination with an effective amount of ancillary polymerase chain reaction reagents.

* * * * *

UNITED STATES PATENT AND TRADEMARK OFFICE
CERTIFICATE OF CORRECTION

PATENT NO. : 5,369,004
DATED : November 29, 1994
INVENTOR(S) : POLYMEROPOULOS et al It is certified that error appears in the above-indentified patent and that said Letters Patent is hereby corrected as shown below:

On the title page, item [56], after the section entitled "U.S. PATENT DOCUMENTS" please insert the following:

--       FOREIGN PATENT DOCUMENTS

| | | |
|---|---|---|
| 92-12262 | 7/1992 | PCT |
| 91-310839 | 8/1991 | European Pat. Off. |
| 91-369603 | 9/1991 | European Pat. Off. |
| 92-21693 | 12/1992 | PCT |
| 92-13101 | 8/1992 | PCT |

--

On the title page, item [56], please add the following under "OTHER PUBLICATIONS":

--Xiao et al. "Abundance of Microsatellite Repeat Sequences in Human Genomic and cDNA Libraries", Am. J. Hum. Genet. Vol 51(4 Suppl) (1992).--

Signed and Sealed this

Twenty-third Day of May, 1995

Attest:

BRUCE LEHMAN

Attesting Officer      Commissioner of Patents and Trademarks